(12) United States Patent
Scheels

(10) Patent No.: US 7,297,510 B2
(45) Date of Patent: Nov. 20, 2007

(54) COMPOSITIONS CONTAINING ENZYMES BOUND TO CATIONIC COPOLYMERS

(75) Inventor: Norman E. Scheels, Monona, WI (US)

(73) Assignee: Genencor International, Inc., Palo Alto, CA (US)

( * ) Notice: Subject to any disclaimer, the term of this patent is extended or adjusted under 35 U.S.C. 154(b) by 439 days.

(21) Appl. No.: 10/472,717

(22) PCT Filed: Apr. 17, 2002

(86) PCT No.: PCT/US02/11963

§ 371 (c)(1),
(2), (4) Date: Sep. 19, 2003

(87) PCT Pub. No.: WO02/083741

PCT Pub. Date: Oct. 24, 2002

(65) Prior Publication Data

US 2004/0121437 A1    Jun. 24, 2004

Related U.S. Application Data

(60) Provisional application No. 60/284,373, filed on Apr. 17, 2001.

(51) Int. Cl.
| | |
|---|---|
| *C12P 1/00* | (2006.01) |
| *C12N 11/14* | (2006.01) |
| *C12N 11/02* | (2006.01) |
| *C12N 11/08* | (2006.01) |

(52) U.S. Cl. .................. 435/41; 435/176; 435/177; 435/180

(58) Field of Classification Search ............ None
See application file for complete search history.

(56) References Cited

U.S. PATENT DOCUMENTS

| 4,141,857 A | 2/1979 | Levy et al. ............. 252/430 |
| 4,438,196 A | 3/1984 | Lantero, Jr. ............. 435/96 |
| 4,918,016 A | 4/1990 | Leuba et al. ............. 435/176 |
| 5,166,064 A | 11/1992 | Usui et al. ............. 435/180 |
| 5,314,810 A | 5/1994 | Kono et al. ............. 435/97 |
| 5,885,609 A | 3/1999 | Amiji ............. 424/425 |

OTHER PUBLICATIONS

International Search Report for PCT/US02/11963.

*Primary Examiner*—David M. Naff
(74) *Attorney, Agent, or Firm*—Jill A. Jacobson

(57) ABSTRACT

Disclosed are a method of adhering active enzymes to an inert support, the product produced thereby, and a method of using the enzyme-coated support in enzyme-catalyzed reactions such as the glucose isomerase-catalyzed conversion of glucose to fructose. The method includes the steps of coating an inert support with a cationic copolymer, preferably a polyamine, and most preferably a di-$C_1$-$C_6$-alkylamino-epichlorohydrin copolymer, and then adhering enzyme to the coated support in the absence of any intervening cross-linking agent.

7 Claims, No Drawings

COMPOSITIONS CONTAINING ENZYMES BOUND TO CATIONIC COPOLYMERS

PRIORITY

This application is a 371 of PCT/US02/11963, filed Apr. 17, 2002, which claims the benefit of Ser. No. 60/284,373 filed Apr. 17, 2001.

FIELD OF THE INVENTION

The invention is directed to a method of immobilizing enzymes on inert supports using cationic copolymers, preferably polyamines. The invention is also directed to the product produced thereby and the use of the product in industrially useful processes that use enzymatically-catalyzed reactions.

BACKGROUND OF THE INVENTION

Enzymes are biological catalysts. They are proteins and are commonly water-soluble. Enzymes are isolated and used in an extraordinarily large and diverse number of commercial applications, including analytical, medical, food-processing, and industrial applications. For example, enzymes are used to prepare food products such as cheese, bread, and alcoholic beverages; enzymes are used to resolve amino acids; enzymes are used in meat tenderizers, detergent formulations, leather tanning agents, and in digestive aids. Enzymes are also used extensively in the processing of starch, such as in starch hydrolysis, sucrose inversion, glucose isomerization, etc. These uses for enzymes, as well as many others, are addressed in great length in the relevant literature.

Enzymes in solution are difficult to recycle while maintaining high catalytic activity. Even without attempting to recycle the enzymes, it is often difficult to maintain high catalytic activity of enzymes for any extended period. These factors often make enzymatic catalysis an expensive proposition due to the necessity to replace the enzyme often.

To minimize the need for replacement, enzymes have been immobilized or otherwise insolubilized on inert supports or carriers. The enzyme remains catalytically active, but because the enzyme is affixed to a solid support, it can be removed from the reaction solution by filtering or screening. By immobilizing the enzyme on a solid support, the enzyme can be recycled more easily and the active useful life of each enzyme batch can be increased.

Immobilized enzymes are used in many different reactor systems, such as in packed columns, stirred tank reactors, fluidized-bed reactors, etc. In general, immobilizing the enzyme provides one or more benefits, including more favorable conditions wherein the enzyme can be used, greater structural stability, increased active life span of the enzyme, minimized effluent problems, minimized material handling problems, and (potentially) increased activity of the enzyme itself.

The patent literature describes a great many means of immobilizing enzymes on an inert support. One general method is to adsorb the enzyme at a solid surface as, for example, when an enzyme such as amino acid acylase is adsorbed on a cellulosic derivative such as DEAB-cellulose; papain or ribonuclease is adsorbed on porous glass; catalase is adsorbed on charcoal; trypsin is adsorbed on quartz glass or cellulose, chymotrypsin is adsorbed on kaolinite, etc.

Another general method to immobilize enzymes is to trap an enzyme in a gel lattice, such as glucose oxidase, urease, papain, etc., being entrapped in a polyacrylamide gel; acetyl cholinesterase being entrapped in a starch gel or a silicone polymer; glutamic-pyruvic transaminase being entrapped in a polyamide or cellulose acetate gel, etc.

A further general method is to use a cross-linking reagent to bind the enzyme to the support. In this approach, bifunctional or polyfunctional reagents that induce intermolecular cross-linking covalently bind the enzymes to the solid support. Glutaraldehyde or bisdiazobenzidine-2,2'-disulfonic acid are conventionally used as cross-linking reagents.

Conventional methods of immobilizing enzymes, however, all possess distinct drawbacks that detract from their use in industrial processes. For example, when an enzyme is directly adsorbed on the surface of a support, the binding forces that result between the enzyme and the support are often quite weak. Consequently, the enzyme is often readily desorbed from the support. Alternatively, the enzyme may be deactivated partially or extensively once immobilized (presumably due to conformational constraints caused by the binding reaction or due to adverse interactions between the support and the active site of the enzyme).

SUMMARY OF THE INVENTION

A first embodiment of the invention is a composition of matter comprising an inert support, a cationic polymer adhered to the inert support, and an enzymatically-active enzyme adhered to the cationic polymer in the absence of any intervening cross-linking agent. The inert support comprises a material selected from the group consisting of silica, alumina, titania, diatomaceous earth, kaolin, glass, organic polymers, and cellulose. An inert support comprising silica is preferred. It is also preferred that he inert support is a particulate material having an average diameter equal to or smaller than about 30 mesh. In the preferred embodiment, the cationic polymer is a polyamine, more preferably still a copolymer comprising a di-$C_1$-$C_6$-alkyl amine co-polymerized with an $\alpha$-halo-$\omega$-epoxy-$C_3$-$C_6$-alkane, such as dimethylaminoepichlorohydrin. The preferred enzyme comprises glucose isomerase.

A second embodiment of the invention is directed to a method of making an enzyme adhered on a support. The method comprises first contacting an inert support with a cationic polymer, whereby the cationic polymer is adhered to the inert support. The inert support is then contacted with an enzyme under conditions wherein the enzyme adheres to the cationic polymer, absent any intervening cross-linking agent.

A third embodiment of the invention is directed to method of performing an enzymatic reaction. Here, the method comprises catalyzing the enzymatic reaction using an enzyme adhered to an inert support as disclosed and claimed herein.

DETAILED DESCRIPTION OF THE INVENTION

The invention thus is directed to a method of securely binding enzymes to an inert support without adversely affecting the catalytic functionality of the bound enzyme.

In general, the first embodiment is drawn to a method of adhering active enzymes to an inert support. The method comprises coating an inert support with a cationic copolymer, preferably a polyamine, and most preferably a di-$C_1$-$C_6$-alkylamino-epichlorohydrin copolymer, and then adhering enzyme to the coated support in the absence of any intervening cross-linking agent.

The second embodiment of the invention is directed to the enzyme-coated inert support. Specifically, the second embodiment of the invention is directed to an inert support having coated thereon a layer of cationic copolymer preferably a polyamine copolymer and most preferably a di-$C_1$-$C_6$-alkylamino-epichlorohydrin copolymer), and a layer of active enzyme directly deposited on top of, or interspersed with, the cationic copolymer, preferably in the absence of any intervening cross-linking agent.

The enzyme-coated support finds utility in virtually any reaction that requires enzymatic catalysis. The preferred use, however, is in the manufacture of high-fructose corn syrup (HFCS) from starch. The starch is obtained from a variety of seed crops, such as corn, wheat, rice, and maize, and root crops such as potato and cassava. The standard of identity for all converted syrups is HFCS. For the production of HFCS, the starch, a polymer, is first hydrolyzed to glucose, its monomeric unit, and the glucose is then isomerized enzymatically to fructose. Fructose is roughly 75% sweeter than sucrose. In the preferred embodiment of the invention, glucose isomerase is adhered to an inert support using a cationic copolymer, preferably a polyamine copolymer. The glucose solution is passed through and/or over the enzyme-coated support, whereby the glucose is enzymatically converted to fructose by the action immobilized GI. The process results in a production stream of HFCS without the inconvenience of having to remove or recycle solution-phase GI. Once the immobilized GI has reached the end of its useful life span, the solid-phase support can easily be removed from the reactor and replaced with new immobilized enzyme.

The nature of the inert support is not critical to the functioning of the invention, so long as the support is, in fact, inert. Several are mentioned in the BACKGROUND section. A large number of such supports are known in the art and can be purchased from several worldwide vendors. Illustrative examples of supports that can be used in the present invention include inert mineral supports, such as silica, alumina, titania, diatomaceous earth, kaolin, etc.; glass supports, such as controlled pore glass; engineered organic-inorganic supports, such as that described in U.S. Pat. No. 4,141,857, issued Feb. 27, 1979 and assigned to UOP, Inc.; organic supports such as polystyrene beads, chlorofluorocarbon beads (e.g., TEFLON-brand polytetrafluoroethylene, NAFION-brand perfluorinated polymer), polyacrylamide gels, cellulose and modified cellulose, and the like. While no support is especially preferred over any other, good results have been achieved using a silica-based product designated R-648 and marketed by World Minerals (Santa Barbara, Calif.), alumina products obtained from UOP (Des Plaines, Ill.), and diatomaceous earth products from Eagle-Picher Mineral Industries (Reno, Nev.). Other commercial suppliers of inert supports include United States Silica (Berkeley Springs, West Va.), Prime Synthesis (Aston, Pa.), CPG, Inc. (Lincoln Park, N.J.), and DuPont Chemical Co. (Wilmington, Del.).

The preferred cationic copolymer for use in the present invention is a polyamine. From among these polyamines, the preferred copolymer is formed from a di-$C_1$-$C_6$-alkyl amine and an α-halo-ω-epoxy-$C_3$-$C_6$-alkane, such as epichlorohydrin (i.e. 1-chloro-2,3-epoxypropane). For sake of expository brevity, the description that follows will be limited to "dialkyaminoepicholorohydrin," with the understanding that this term also extends to homologs thereof (e.g., copolymers of a di-$C_1$-$C_6$-alkyl amine and 1-halo-3,4-epoxybutane, 1-halo-4,5-epoxypentane, etc.) Thus, these copolymers are collectively designated herein as dialkylaminoepicholorohydrin copolymers. Structurally, such copolymers appear as follows:

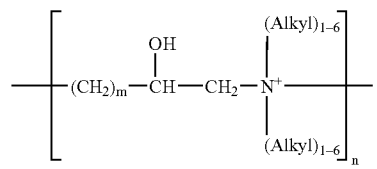

where m is an integer of from 1 to 4 and n is an integer that yields a copolymer having a molecular weight of from approximately 10,000 Da to greater than 1,000,000 Da.

The specific copolymer formed between a di-$C_1$-$C_6$-alkyl amine and 1-halo-2,3-epoxypropane has the following structure:

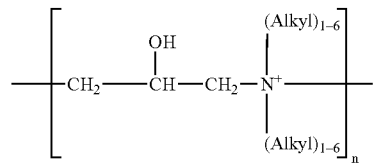

Such copolymers are easily manufactured by combining a dialkylamine with a α-halo-ω-epoxy-$C_1$-$C_6$-alkane, such as epichlorohydrin, in the presence of excess base. Copolymers having a molecular mass of anywhere from about 10,000 Da to more than $1\times10^6$ Daltons are readily attainable by this route. Note that because of the quaternized nitrogen atoms in the polymer backbone, these copolymers are distinctly cationic.

Dialkyaminoepicholorohydrin copolymers are also available commercially. The preferred commercial copolymer is sold under the trademark CYSEP by Cytec Industries (West Patterson, N.J.). The preferred formulation is designated CYSEP-349, although any of the copolymers in CYSEP-branded line will function. The CYSEP-349 copolymer has a molecular mass of roughly 250,000 Da. Currently, the following additional CYSEP-branded dialkylaminoepicholorohydrin copolymers can be obtained from Cytec Industries: CYSEP-572, CYSEP-573, CYSEP-577, CYSEP-581, CYSEP-587, and CYSEP-591. The product is usually delivered in solution form, with a solids level between about 10 and 50%, depending on the molecular mass.

A sampling of the sizes of the CYSEP-branded products is given in the following table:

| Name | Mass (Da) | Comments |
|---|---|---|
| C-349 | 250,000 | High purity, for food industry |
| C-572 | 40,000 | |
| C-573 | 50,000 | |
| C-577 | 80,000 | |
| C-581 | 250,000 | Less pure version of C-349 |

There are many distinct advantages to the inventive method described herein as compared to conventional means for adhering enzymes to solid supports. Conventionally, an enzyme (such as glucose isomerase) is adhered to a support in a two-step process using polyethylenimine (PEI) and a bi-functional cross-lining reagent such as glutaraldehyde (GTA). In the preferred embodiment of the invention, the need for two reagents is eliminated; the enzyme can be firmly adhered to the inert support using only the cationic polymer. The present invention does not exclude the use of a cross-linker such as GTA; but the use of a cross-linker is not preferred.

Another advantage of the present invention is that the presence of quaternary ammonium groups within the backbone of the copolymer molecule ensures that it maintains its very strong cationic charge throughout the pH range of most industrial, and notably, most food-processing operations. While not being bound by any particular interpretation or mechanism, it is believed that this intense cationic charge contributes to the strong bound activity seen in the enzyme-coated supports described herein.

Implementation of this invention will immediately result in the replacement of the existing PEI/GTA binding procedure in the manufacture of immobilized glucose isomerase (and other enzymes) with one requiring the use of a dialkylaminoepichlorohydrin copolymer. This will lower the overall cost of bound glucose isomerase by both increasing the binding efficiency of the enzyme to the support and reducing the cost of raw materials.

The method to coat the inert support is straightforward. As noted above, while the nature of the support is not critical to the invention, the preferred carrier for binding is a silica product marketed by World Minerals under the designation R-648. This product combines the desirable attributes of adequate surface area, pore size and overall mechanical toughness. Equally preferred are any number of alumina products manufactured by UOP (several have already been tested with good results) and a diatomaceous earth product from Eagle-Picher (this has also been tested with good results).

All inert supports that have been evaluated thus far have been delivered with a small percentage of dust material. These fines, probably generated during shipment, are removed on the lab bench through a series of batch-agitated rinse steps. In production, the fines are removed by an upflow rinse through the fluidized bed of carrier.

The residual rinse water is decanted from the settled carrier. The carrier is then recharged with water and dosed with a solution of copolymer. The copolymer is represented in grams on an as-is basis to the carrier, also on a weight basis, or % wt/wt. The copolymer dosing generally ranges from between about 2 to about 50%, and more preferably from about 7 to about 22%. Percentages above and below these ranges are encompassed by the invention. However, the stated ranges strike a good balance between achieving maximum bound activity and minimum use of the copolymer. The solution is vigorously mixed for about 2 hours, and then allowed to settle. After decanting the residual copolymer solution from the carrier, the carrier is rinsed at least three times (when making small batches on a lab bench) or subjected to continuous flow rinse in a production column.

At this point, a layer of copolymer has been applied to the carrier. The next step is either to attach the enzyme directly onto the copolymer layer in the absence of any intervening cross-linking layer (preferred) or adding a cross-linking layer, such as a layer of glutaraldehyde, on top of the copolymer layer (less preferred). As shown in the Examples below, the incremental benefit of using a cross-linking layer on top of the copolymer is small when binding glucose isomerase. Nevertheless, the invention encompasses the use of a cross-linking agent. While the invention encompasses using a cross-linking layer, in the preferred embodiment, the enzyme is bound directly to the copolymer layer, in the absence of any intervening layer.

While some experiments performed to date support the conclusion that a cross-linking layer enhances the quality of the binding of the enzyme to the support, the real question is whether the incremental improvement is economical in light of the extra cost and effort of including the cross-linking step. If a cross-linking step is used, the 100% equivalent glutaraldehyde dose varies between about 5% and 12% (wt/wt) of the starting dry carrier weight. The copolymer-coated support and the cross-linker are agitated for about 2 hours, and the remaining solution decanted. The treated support is rinsed as described about to remove any of the residual, non-bound glutaraldehyde before applying the enzyme to the support.

The quantity of enzyme added to the support will depend primarily upon the quality of the carrier in terms of its ability to hold activity. For purposes of the discussion that follows, the enzyme used was glucose isomerase (available commercially from Enzyme Bio-Systems Ltd., Beloit, Wis.). This is for purposes of brevity and clarity only. The subject invention will work with any proteinaceous material, without limitation, including non-enzymatic proteins.

Using glucose isomerase (GI) as the enzyme, carriers having bound activity ranging from between 0.82 and 1.09 U/g dry basis of carrier have been made. Because GI solutions are assayed as to their activity in units per milliliter, the total carrier weight and liquid enzyme activity can be used to calculate the total volume required. Additionally, magnesium salt in the form of either magnesium sulfate or magnesium chloride is added to a level of about 100 ppm magnesium atom basis. When binding glucose isomerase, the binding solution should have a pH between about 6 and 9, more preferably between about 6.2 to about 8.5. The pH of the binding solution can be adjusted with either dilute caustic or hydrochloric acid. In practice, such pH adjustment is not necessary as the solution normally falls within this range.

The optimal pH for binding other proteins will vary, of course. The optimum pH, however, is easily determined based upon the isoelectric point of the enzyme and the known functional properties of the enzyme itself. That is, the optimum pH of the binding solution generally coincides with the pH that is optimum for enzyme activity. Such data is already known for a great many enzymes, and can be determined a priori by those skilled in the art for newly discovered enzymes. Thus, the optimum pH of any enzyme is determined by assaying the activity of the enzyme in solutions of various pH's. The isoelectric point of a protein is the pH at which there is no net electric charge on the protein. The isoelectric point is determined electrophoretically; at the isoelectric pH, the protein has no mobility in the gel (because the protein has no net charge).

When using glucose isomerase, exposure time to the binding solution is generally from about 4 to about 8 hours at a temperature between about 15° C. (59° F.) and about 60° C. (140° F.). After settling and decanting the reaction solution, the newly bound carrier is rinsed with a sodium chloride (NaCl) solution having a concentration of between about 1.0 to 5.0%, rinsed with water, and then packed in a stabilizing solution, such as a 20% glycol solution.

EXAMPLES

The following Examples are included to provide a more clear and consistent understanding of the subject invention. The Examples do not limit the scope of the invention described herein in any fashion.

Example 1

This Example compares the results of four different binding protocols: one using PEI and GTA in conventional fashion, one using CYSEP-349-brand copolymer and GTA, and two protocols using only the copolymer. Protocols 1 and 2 included 1.5% salt and were dosed to 1.27 U/g glucose isomerase.

Protocol no. 1 used PEI as the binding layer while protocol no. 2 used CYSEP-349 copolymer. Both were used at 22 g per 150 g support. The PEI was in the form of a 35% (wt/wt) solution; the CYSEP-349 copolymer solution was used as delivered from the manufacturer (determined to be a 50% (wt/wt) solution). The results of protocols 1 and 2 normalized to standard PEI/GTA production were as follows.

| Binding Protocol | Bound (U/g) | Decant (U/g) | After 5% Salt Wash: Bound (U/g) | 5% Salt Wash: Decant (U/g) |
|---|---|---|---|---|
| 1) PEI/GTA/GI | 1.0 | 3.0 | 1.04 | 0.31 |
| 2) CYSEP/GTA/GI | 1.23 | 1.52 | 1.24 | 0.89 |

Protocols 1 and 2 show that binding with the copolymer leads to superior activity as compared to conventional PEI/GTA binding both before and after the salt wash. The salt wash increased the bound enzyme activity in both protocols.

The value of the salt wash is indicated above. The position within the protocol is important. As can be see in the next example, mixing salt with the enzyme during the binding process was not fruitful. This example includes no glutaraldehyde.

| Test | Bound Activity | Decant Activity | After 5% Salt Wash Bound Activity | 5% Salt Wash Decant Act. |
|---|---|---|---|---|
| 3) CYSEP/GI + salt | 1.26 | 1.38 | 1.10 | 1.22 |
| 4) CYSEP/GI | 1.33 | 1.22 | 1.10 | 1.22 |

The results obtained in protocols 3 and 4 were very surprising in that supports coated only with CYSEP-349-brand copolymer exhibited very high levels of bound enzyme activity: 1.33 U/g before washing with salt and 1.10 U/g after the salt wash.

Example 2

This Example illustrate the effect achieved by the use of GTA in the binding protocol. Two samples were bound with the CYSEP/GTA procedure and two with CYSEP only. The enzyme dosage was 0.91 U/g of dry carrier normalized to customary production dosage. One sample from each of the duplicate samples from each grouping was given a 5% salt wash for 2 hours, while the other duplicate had a salt treatment during binding. Batch assays were then run on all of the samples, with the following results obtained:

| Binding Protocol | Bound Activity (U/g) |
|---|---|
| CYSEP/GTA/GI | 1.23 |
| As Above + Salt Wash | 0.94 |
| CYSEP/GI | 1.24 |
| As Above + Salt Wash | 0.96 |

The results from this Example reveal two discoveries:
1) The use of GTA in the binding protocol has little or no effect on the ultimate bound activity achieved; and
2) A salt wash appears to remove extraneous, poorly bound activity. Note that the loss of activity due to the salt wash is the same whether or not GTA is used. Thus, this Example shows that GTA can be eliminated from the binding protocol, yet a very high bound activity was still achieved.

Example 3

This Example investigated how much copolymer is required to bind GI efficiently and effectively. As in Example 1, a 150-g sample of R-648 was mixed with 22 g of CYSEP-349 copolymer. The CYSEP solution was used as delivered by the manufacturer, which is a 50% (wt/wt) solution. In this Example, GTA was used, at a dosage of approximately 8% by wt. All tests used an enzyme dosage of 1.27 U/g. The results, based upon 150 g of R-648 are shown below:

| CYSEP (% ds) | Bound Activity (U/g) |
|---|---|
| 2.2 | 0.57 |
| 3.1 | 0.68 |
| 7.0 | 1.16 |
| 7.35 | 1.17 |
| 14.7 | 1.13 |
| 22.0 | 1.18 |

This Example shows that the amount of bound activity essentially levels off at approximately 7.0% copolymer. Increased levels of copolymer did not yield a corresponding increase in bound activity.

Example 4

This Example shows the results of enzyme dosage isotherm data when using CYSEP-349 copolymer.

The isotherm data were collected over a roughly 3-month period. Bindings were conducted on a laboratory scale with CYSEP-349 copolymer as the essential binding agent. Samples were taken both with and without a salt wash, and with and without a cross-linker (GTA). The salt concentration, when used, was 1.5% (wt/vol).

| Dose | GTA + salt Aug. 31, 2000 | GTA + salt Oct. 20, 2000 | GTA + salt Oct. 18, 2000 | no GTA + salt Oct. 24, 2000 | GTA no salt Oct. 14, 2000 | no GTA no salt Oct. 11, 2000 |
|---|---|---|---|---|---|---|
| | | | Activity, (U/g) | | | |
| 0.64 | 0.96 | 0.90 | 0.92 | 0.83 | 0.83 | 0.89 |
| 0.91 | 1.24 | 1.23 | 1.18 | 1.09 | 1.06 | 1.16 |
| 1.18 | 1.24 | 1.45 | 1.41 | 1.24 | 1.22 | 1.39 |
| 1.45 | 1.26 | 1.54 | 1.47 | 1.44 | 1.26 | 1.52 |

The above data was then compared with a typical isotherm run with PEV/GTA and no salt. See the table that follows. Also included are the results obtained using another CYTEC brand polymer, Magnafloc 718. In addition to the epichlorohydrin and dimethylamine found in CYSEP-349, this copolymer also has ethylenediamine to provide cross-linking. The results are below:

| Dosage (U/g) | PEI/GTA Protocol Bound Activity (U/g) | Magnifloc 718 Bound Activity (U/g) |
|---|---|---|
| 0.36 | 0.42, 0.64 | — |
| 0.54 | 0.71 | — |
| 0.72 | 0.81, 094 | 0.98 |
| 0.91 | — | 1.05 |
| 1.09 | 0.71, 0.94 | 1.14 |
| 1.27 | — | 1.14 |
| 1.45 | 0.96, 1.12 | — |

All the CYSEP-349 copolymer trials generated data that compare favorably with earlier work done on PEE systems. In addition, it appears that the CYSEP alone, without GTA, binds as well as CYSEP with GTA. Any observed difference in bound activity is more than made up by the reduced cost and time achieved by eliminating the need for GTA.

Example 5

This Example shows that the invention can be practiced using copolymers of different molecular weights. A comparison with the conventional PEI/GTA protocol is also included. All samples were dosed to 0.91 U/g glucose isomerase.

| Name | Mass (Da) | Bound Activity, Pre Salt Wash (U/g) | Bound Activity, Post Salt Wash (U/g) |
|---|---|---|---|
| PEI/GTA | | 0.97 | 0.89 |
| PEI only | | 1.11 | 0.26 |
| C349/GTA | 250,000 | 1.30 | 1.06 |
| C349 only | 250,000 | 1.52 | 1.03 |
| C577/GTA | 80,000 | 1.24 | 1.01 |
| C577 only | 80,000 | 1.35 | 0.82 |
| C573/GTA | 50,000 | 1.20 | 0.94 |
| C573 only | 50,000 | 1.22 | 0.83 |
| C572/GTA | 40,000 | 1.31 | 1.03 |
| C572 only | 40,000 | 1.33 | 0.88 |

As shown in the table, all of the CYSEP-treated samples tested exhibited higher initial activity when used in the absence of a cross-linker GTA. CYSEP-349 had the highest post-salt wash activities, both with and without GTA. The difference between the GTA-treated and non-GTA treated CYSEP-349 was negligible.

Example 6

This example is identical to that described in Example 1, with the exception that a different support was used: a diatomaceous earth product designated MP-79 (Eagle-Picher). This product, MP-79, is readily available commercially. It is marketed as an oil absorbent and cat litter. This product has much less surface area that the material used in examples previously.

All MP-79 samples were screened to approximate the size distribution found in the R-648 carrier. This eliminates particle size as a potential difference between the two carriers.

In the following table, the amount bound is reported after rinsing. The free amount is that found in the wash. The "Total" represents the amount of the loading that is accounted for in the measurement of that bound and free.

| Dose (U/g ds) | PEI/GTA Bound U/g | PEI/GTA Free | PEI/GTA Total % | CYSEP-349/GTA Bound U/g | CYSEP-349/GTA Free | CYSEP-349/GTA Total % | CYSEP-349 only Bound U/g | CYSEP-349 only Free | CYSEP-349 only Total % |
|---|---|---|---|---|---|---|---|---|---|
| 0.36 | .35 | .6 | 92 | .52 | .3 | 90 | .47 | .11 | 82 |
| 0.72 | .45 | 1.53 | 81 | .56 | 1.75 | 97 | .72 | 1.0 | 85 |
| 1.09 | .55 | 2.8 | 85 | .6 | 3.06 | 92 | .88 | 2.1 | 89 |
| 1.45 | .58 | 3.8 | 80 | .61 | 4.49 | 91 | .88 | 3.6 | 90 |

The binding time was 4 hours. MP-79 functions quite well as a support, using only CYSEP to adhere the enzyme to the support.

Example 7

As an example of the applicability of the method to other carriers, a test was run with a crushed alumina product supplied from UOP. Four samples, 90 g each, were treated with 13.2 g of an epichlorohydrin-dimethylamine copolymer solution for 2 hours. These were rinsed with water and exposed to glucose isomerase at the concentrations noted in the table below. After four hours exposure, the carrier was rinsed with water. The amount of bound activity and the amount in the final water rinse is noted below.

| Dose (U/g) | Bound Enzyme (U/g) | Enzyme in Decant (U/g) |
|---|---|---|
| .72 | 0.61 | 0 |
| 1.09 | 0.83 | 0.2 |
| 1.45 | 2.0 | .11 |
| 1.82 | 2.11 | .07 |

The epichlorohydrin-dimethylamine system gives activities equivalent to or greater than comparable activities obtained using PEI and GTA.

Example 8

All bindings tested in Examples 1-7 used de-ionized (DI) water as the solvent. This Example addresses whether the quality and source of the water influences the results. Specifically, this Example explores how DI compares to other waters such as raw (well water), softwater, and reverse osmosis water (RO), which is used as boiler feed water.

Every binding step in this Example was completed in its entirety with the water selected for evaluation. This included all rinse steps, CYSEP treatment, and the enzyme application solution.

Dry carrier in the amount of 150 grams was rinsed and then treated with 15% w/w epichlorohydrin-dimethylamine copolymer (as-is) diluted in 800 ml of the test water for 2 hours. Following further rinses, the carrier was agitated in a GI solution having an equivalent dosage of 1.0 units/g carrier. This procedure was then terminated after 4 hours with three more rinses. Each type of water was tested twice:

| Water | Bound Activity |
|---|---|
| Raw | 1.12 |
|  | 1.14 |
| Soft water | 1.14 |
|  | 1.15 |
| Reverse Osmosis Water | 1.12 |
|  | 1.08 |
| De-ionized Water | 1.20 |
|  | 1.22 |

As shown in the above table, the binding procedure proceeds successfully using any source of reasonably clean water. While the first three types of water appear to be equivalent, it is apparent that using DI water results in superior activity.

Because the epichlorohydrin-dimethylamine copolymer molecule contains heavily charged sites, it is hypothesized that high ionic activity in the water could interfere with its attachment to the carrier. This is tested below by dosing de-ionized water with increasing concentrations of NaCl, and then using this water as the solvent in copolymer application to the R-648.

Each salt solution was tested only in the CYSEP application step. All other procedures used laboratory de-ionized water. All other parameters remained the same, including the enzyme dosage at 1.0 and the 2-hour binding time.

| NaCl (ppm) | Bound Activity |
|---|---|
| 0 (DI) | 1.25 |
| 500 | 1.19 |
| 5000 | 0.78 |
| 50,000 | 0.47 |

Only the CYSEP attachment step was with salt water, all other binding steps were with DI. Therefore it can be assumed that through some mechanism of ionic interference, CYSEP does not attach as well in high ionic strength solutions as it does in waters made more pure. Therefore, even though this binding process will work using water solvents of any ionic strength, it is preferable that the water be as pure as possible.

Example 9

Binding will take place using the subject invention when using several types and suppliers of granular carbon: Dry carrier in the amount of 150 grams was rinsed and then treated with 15% w/w epichlorohydrin-dimethylamine copolymer (as-is) diluted in 800 ml of the test water for 2 hours. In some cases glutaraldehyde was applied on top of the CYSEP by agitating for 2 hours in 800 ml of a 1.8% solution for two hours.

Following another set of rinses, the carrier was agitated in a GI solution having an equivalent dosage of 1.0 units/g carrier. This procedure was then terminated after 4 hours with another set of rinses.

Carbon binding was also attempted without the aid of any chemical aid with the results below:

| Carbon | Bound Activity |
|---|---|
| Calgon/CYSEP Only | 0.33, 0.31, 0.33, 0.35 |
| R-648/CYSEP Control | 1.18 |
| Chemsorb 1000-60/CYSEP/GTA | 0.0073 |
| Carbon/CYSEP | 0.02 |
| Carbon Only | 0.03 |
| R-648/CYSEP Control | 1.15 |
| Carbochem 1000/CYSEP/GTA | 0.03 |
| Carbon/CYSEP | 0.07 |
| Carbon Only | 0.03 |

These results demonstrate that carbon will bind enzyme, albeit to a limited extent. Inferiority to R-648 is apparent. Interestingly enough, carbon by itself, without chemical aids, seems to bind better that it does when CYSEP or GTA or both are used. This suggests that particle pore size is an issue. Even though the surface area of the carbon substrate is much greater than that of the other carriers tested, presumably it comes at the price of pores too small to permit entry of enzyme.

Example 10

This Example addresses the optimum length of time the enzyme applications should take. Dry carrier in the amount of 150 grams was rinsed and then treated with 15% w/w epichlorohydrin-dimethylamine copolymer (as-is) diluted in 800 ml of the test water for 2 hours.

Leaving all pretreatment rinses the same and using CYSEP only, four R-648 samples were dosed to 1.0 units/gram and agitated in an enzyme solution for the following indicated periods of time:

| Binding Time | Bound Activity |
| --- | --- |
| ½ hour | 0.80 |
| 1 hour | 0.94 |
| 4 hours | 1.12 |
| 8 hours | 1.125 |

From these data, it appears that maximum enzyme binding occurs within 4 hours. Although shorter binding times will also yield positive activity results, four hours is the optimum exposure time of the enzyme to the carrier under the conditions tested. Additional exposure time did not result in significantly greater bound acitvity.

Example 11

Efforts to increase the surface area (and hence the binding efficiency) of the R-648 carrier would presumably bear fruit in terms of increased bound activities. In this Example, three acid and chelant chemical pre-treatments were compared with an untreated control. These treatments were designed to scour the carrier surface and thus increase the carrier porosity.

Following the chemical treatments, each carrier sample, in the amount of 150 grams, was rinsed and then treated with 15% w/w epichlorohydrin-dimethylamine copolymer (as-is) diluted in 800 ml of the test water for 2 hours. Following another set of rinses, the carrier was agitated in a GI solution having an equivalent dosage of 1.0 units/g carrier. This procedure was then terminated after 4 hours with another set of rinses.

| Treatment | Bound Activity |
| --- | --- |
| R-648 | 1.02 |
| R-648 + 1% citric acid for 2 hours | 1.26 |
| R-648 + 0.125% EDTA for 2 hours | 1.05 |
| R-648 + 0.625% citric and 0.125% EDTA for 2 hours | 1.25 |

Although binding readily takes place regardless of any of these pre-treatments, using a citric acid soak results in enhanced bound activity.

Example 12

A calcined amalgam of bentonite clay and diatomaceous earth was tested as the substrate. This material, called PLAYBALL (from Eagle-Picher), is normally used to condition the dirt of wet baseball infields following inclement weather. Its relatively low price makes it attractive compared with other carriers.

The standard testing procedure was followed. Dry carrier in the amount of 150 grams was rinsed then treated with 15% w/w epichlorohydrin-dimethylamine copolymer (as-is) diluted in 800 ml of the test water for 2 hours. Following another set of rinses, the carrier was agitated in a GI solution having an equivalent dosage of 1.0 units/g carrier. This procedure was then terminated after 4 hours with another set of three rinses.

CYSEP by itself was compared with earlier work on a similar product called MP-79. All tests were accompanied by R-648 controls. A summary of the statistics are as follows:

| Sample | # Tests | Average Bound Activity | Standard Deviation |
| --- | --- | --- | --- |
| R-648 | 6 | 1.23 | 0.13 |
| MP-79 | 16 | 0.90 | 0.16 |
| PLAYBALL | 11 | 0.98 | 0.11 |

In terms of final bound activity, the R-648 is clearly superior. However, the PLAYBALL product demonstrated a remarkable ability to bind enzyme, as well as good consistency as seen by its low standard deviation.

Example 13

The following are the bound activities of PLAYBALL product samples treated for 1.5 hours with increasing concentrations of citric acid prior to enzyme coating.

Following citric acid pre-treatments, the 150 g of carrier was rinsed and then treated with 15% w/w epichlorohydrin-dimethylamine copolymer (as-is) diluted in 800 ml of the test water for 2 hours. Following another set of rinses, the carrier was agitated in a GI solution having an equivalent dosage of 1.0 units/g carrier. This procedure then terminated after 4 hours with another set of rinses.

| Citric Acid Concentration | Bound Activity |
| --- | --- |
| 0% (No acid wash) | 0.89 |
| 0.5% | 0.95 |
| 2.0% | 0.90 |
| 5.0% | 0.89 |

These results are not as clear cut as they were in the prior Example when R-648 was acid washed. There is some hint that a mild wash will improve enzyme binding, but the improvement is not nearly as dramatic as it is when R-648 is the carrier.

Example 14

Next, a more premium, silica-based, chromatography-grade support, called Matrex (Amnicon) was evaluated. The dry test carrier in the amount of 150 grams was rinsed and then treated with 15% w/w epichlorohydrin-dimethylamine copolymer (as-is) diluted in 800 ml of the test water for 2 hours. Following another set of rinses, the carrier was agitated in a GI solution having an equivalent dosage of 1.0 units/g carrier. This procedure was then terminated after 4 hours with another set of rinses.

This treatment yielded the following results:

| Sample | Bound Activity |
|---|---|
| R-648 | 1.33 |
| Matrex | 2.16 |

Clearly a fundamental difference in quality exists. However, from a practical and economic standpoint, the Matrex-brand support is a top-of-the-line carrier used primarily in chromatography labs. Thus its use in production environments is difficult to justify economically.

Example 15

The Example investigated the ability of the present approach to bind enzymes other then GI. Here, increasing concentrations of glucoamylase enzyme was exposed to R-648 which had been pretreated with CYSEP-349. The following isotherm was generated:

| GA dosage U/g | Bound Activity |
|---|---|
| 10 | 2.0 |
| 50 | 6.5 |
| 100 | 20.5 |
| 200 | 21.2 |

The apparent carrying capacity of R-648 using epichlorohydrin-dimethylamine copolymer binding agent is about 20 to 21 units per gram carrier, clearly demonstrating that the method of the present invention will work with other enzymes.

Example 16

In Examples 1-15, Cytek Corporation was the supplier of the epichlorohydrin-dimethylamine copolymer used. There are other suppliers of the copolymer, including Ashland Chemical (Columbus, Ohio). Ashland sells epichlorohydrin-dimethylamine copolymer under the trademarks Amerfloc 425E and Amerfloc 485. When used in place of the CYSEP product, and following the exact same binding procedure used in the previous Examples, the Ashland product compares favorably with the CYSEP-349 product:

| Binding Agent | Bound Activity |
|---|---|
| CYSEP-349 | 1.45 |
| Amerfloc 425E | 1.47 |
| Amerfloc 485 | 1.37 |

Example 17

All of the previous Examples treated the support with the epichlorohydrin-dimethylamine prior to exposure to enzyme. This Example set out to determine if the support could be coated by mixing the enzyme together with the copolymer and then applying the mixture to the support. Four different dosages of enzyme were used corresponding roughly to 0.3, 0.6, 0.9 and 1.2 units per gram carrier.

| Dosage | Bound Activity |
|---|---|
| 0.3 | 0.1 |
| 0.6 | 0.12 |
| 0.9 | 0.13 |
| 1.2 | 0.13 |

Although it can be made to work, these results are far inferior to the 1.2 to 1.4 units of bound activity found when attaching the epichlorohydrin-dimethylamine copolymer separately.

Example 18

Earlier patent work using PEI (polyethyleneamine) as the binding agent followed by GTA (glutaraldehyde) as a crosslinking agent postulated the existence of a plastic affixing layer of PEI upon which is attached pendant arms of GTA. GTA is not a large molecule and therefore cannot have very long "arms." This Example investigated what would happen if instead of attaching the CYSEP-349 directly to the carrier, a PEI layer was applied first. The great length of the CYSEP-349 molecule would presumably yield pendant "arms" much longer than those of GTA, and hence (presumably) better able to grab enzyme.

Each of four samples of R-648 carrier were given a preliminary PEI treatment. The dosage of CYSEP remained unchanged among the four tests. The extent of this PEI treatment is given in a fraction of the CYSEP-349 treatment in the data below:

| PEI/CYSEP | Bound Assay |
|---|---|
| 0 | 1.35 |
| 0.32 | 1.33 |
| 0.64 | 0.96 |
| 1.0 | 0.99 |

Although combining PEI with CYSEP in this fashion will lead to reasonable results, it is more effective if CYSEP is used by itself.

Example 19

The Example explored applying PEI and CYSEP as a mixture. Here, the PEE dosage was held constant and the amount of CYSEP admixed with the CYSEP was systematically increased. The results were as follows:

| PEI/CYSEP | Bound Assay |
|---|---|
| 1.0/0 | 1.0 |
| 1.0/0.4 | 0.85 |
| 1.0/0.67 | 0.81 |
| 1.0/1.0 | 0.78 |

Binding will occur, but not to the extent seen using CYSEP alone.

Example 20

Samples of R-648 were screened to three sizes then bound using CYSEP-349. All were compared to a control sample of R-648. CYSEP-349 was applied in an aqueous solution for two hours followed by a four-hour enzyme application period. The binding data according to size was as follows:

| Screen Size | Bound Activity |
|---|---|
| +30 mesh | 1.04 |
| −30 + 50 mesh | 1.42 |
| +50 mesh | 1.53 |
| R-648 Control | 1.28 |

The difference in binding efficiency is clearly dependent upon the carrier particle size when that carrier is R-648.

Binding efficiency changes vs. particle mesh size were investigated using the PLAYBALL carrier. Work with R-648 clearly demonstrated that physically smaller carrier particles yielded higher activities on a per weight basis. PLAYBALL was screened and tested as follows:

| Screen Size | Bound Activity |
|---|---|
| +30 | 0.7 |
| −30 to +50 | 0.9 |
| −50 | 0.83 |

Unexpectedly, the dramatic difference in binding activity with size did not materialize nearly to the extent using the PLAYBALL carrier as it did with R-648.

A sample of R-648 was compared with two alumina products; Alusil 70 and ABA-7000 from Selecto Scientific Inc. (Suwanee, Ga.) and a zeolite sample obtained from GSA with the following results. Dry carrier in the amount of 150 grams was rinsed and then treated with 15% w/w epichlorohydrin-dimethylamine copolymer (as-is) diluted in 800 ml of the test water for 2 hours. Following another set of rinses, the carrier was agitated in a GI solution having an equivalent dosage of 1.0 units/g carrier. This procedure was then terminated after 4 hours with another set of rinses.

| Sample | Bound Activity |
|---|---|
| R-648 | 1.23 |
| Alusil 70 | 0.028 |
| ABA-7000 | 0.16 |
| Zeolite | 0.09 |

This again demonstrates that binding glucose isomerase enzyme with this procedure will work with a wide variety of substrates.

Example 21

A commercial brand of GI, "Spezyme"-brand (Genencor, Palo Alto, Calif.), was compared to a commercially-available GI from Enzyme Bio-Systems (Beloit, Wis.). R-648 was coated with the Spezyme-brand product as described in Example 20. The binding dosages, decant activities and bound activities were as follows:

| Dosage | Decant | Bound |
|---|---|---|
| 500 | 0 | 194 |
| 1000 | 5 | 382 |
| 1500 | 14 | 463 |
| 2000 | 31 | 541 |
| 3000 | 195 | 670 |
| 4000 | 203 | 740 |

The bound activity values for the Genencor GI are quite comparable to those for the Enzyme Bio-Systems GI.

What is claimed is:

1. A composition of matter comprising:
   an inert support;
   a cationic dialkylaminoepicholorohydrin copolymer comprising a di-$C_1$-$C_6$-alkyl amine co-polymerized with an $\alpha$-halo-$\omega$-epoxy-$C_3$-$C_6$-alkane and homologs thereof adhered to the inert support; and
   an enzymatically-active enzyme adhered to the cationic dialkylaminoepicholorohydrin copolymer in the absence of any intervening cross-linking agent.

2. The composition of claim 1, wherein the inert support comprises a material selected from the group consisting of silica, alumina, titania, diatomaceous earth, kaolin, glass, organic polymers, and cellulose.

3. The composition of claim 1, wherein the inert support comprises silica.

4. The composition of claim 1, wherein the inert support is a particulate material having an average diameter equal to or smaller than about 30 mesh.

5. The composition of claim 1, wherein the inert support is a particulate material having an average diameter equal to or smaller than about 50 mesh.

6. The composition of claim 1, wherein the enzyme comprises glucose isomerase.

7. A method of performing an enzymatic reaction comprising catalyzing the enzymatic reaction using an composition of matter as recited in claim 1.

* * * * *